United States Patent [19]

Mathis et al.

[11] Patent Number: 5,279,943
[45] Date of Patent: Jan. 18, 1994

[54] HOMOGENEOUS PROCESS FOR THE DETECTION AND/OR DETERMINATION BY LUMINESCENCE OF AN ANALYTE IN A MEDIUM IN WHICH IT MAY BE PRESENT

[75] Inventors: Gérard Mathis, Bagnoles-Szceze; Thierry Davin, Lapalud, both of France

[73] Assignee: Compagnie Oris Industrie, Paris, France

[21] Appl. No.: 5,610

[22] Filed: Jan. 19, 1993

Related U.S. Application Data

[63] Continuation of Ser. No. 700,106, May 8, 1991, abandoned, which is a continuation of Ser. No. 550,219, Jul. 10, 1990, abandoned, which is a continuation of Ser. No. 45,059, Mar. 31, 1987, abandoned.

[30] Foreign Application Priority Data

Aug. 2, 1985 [FR] France .................................. 85 11905

[51] Int. Cl.$^5$ .......................... C12Q 1/02; C12Q 1/25; G01N 33/536
[52] U.S. Cl. ......................... 435/7.32; 422/61; 435/7.23; 435/7.4; 435/7.5; 435/968; 435/975; 436/536; 436/537; 436/811; 436/813; 436/817
[58] Field of Search ................ 436/525, 537, 546, 800, 436/808, 813, 817, 805, 811, 536; 422/61; 435/7.32, 7.23, 7.4, 7.5, 968, 975

[56] References Cited

U.S. PATENT DOCUMENTS

| | | | |
|---|---|---|---|
| 3,996,345 | 12/1976 | Ullman et al. | 424/12 |
| 4,133,873 | 1/1979 | Noller | 424/8 |
| 4,238,195 | 12/1980 | Boguslaski et al. | |
| 4,261,968 | 4/1981 | Ullman et al. | 424/8 |
| 4,277,437 | 7/1981 | Maggio | 422/61 |
| 4,283,382 | 8/1981 | Frank et al. | 424/8 |
| 4,318,707 | 3/1982 | Litman et al. | 424/8 |
| 4,374,925 | 2/1983 | Litman et al. | |
| 4,587,223 | 5/1986 | Soini et al. | 436/536 |
| 4,637,985 | 1/1987 | Sioki et al. | 436/518 |
| 4,650,770 | 3/1987 | Liu et al. | 436/523 |
| 4,735,907 | 4/1988 | Schaeffer et al. | 436/534 |

FOREIGN PATENT DOCUMENTS

0015695 2/1980 European Pat. Off. .
0103558 9/1983 European Pat. Off. .

Primary Examiner—Jill A. Johnston
Attorney, Agent, or Firm—Woodcock Washburn Kurtz Mackiewicz & Norris

[57] ABSTRACT

The present invention relates to a homogeneous process for the detection and/or determination of an analyte in a medium in which it may be present, by disclosing the reaction product of the analyte and a corresponding receptor, process consisting in: 1) adding to said medium a first reagent consisting of a receptor for the said analyte; 2) adding a second reagent consisting of at least one of the components of the reaction product of the analyte and at least one of its receptors; one of the two reagents being coupled with a luminescent compound and the other reagent possessing a heavy atom or units containing a heavy atom; 3) incubating the medium after addition of each reagent or after the addition of both reagents; 4) exciting the resulting medium and 5) measuring at equilibrium or during the kinetics, the signal emitted by the luminescent compound, said signal being modulated by the heavy atom effect.

22 Claims, 2 Drawing Sheets

HOMOGENEOUS PROCESS FOR THE DETECTION AND/OR DETERMINATION BY LUMINESCENCE OF AN ANALYTE IN A MEDIUM IN WHICH IT MAY BE PRESENT

This application is a continuation of application Ser. No. 700,106, filed May 8, 1991, now abandoned, which is a continuation of application Ser. No. 550,219, filed Jul. 10, 1990, now abandoned, which is a continuation of application Ser. No. 045,059, filed Mar. 31, 1987, now abandoned.

The present invention relates to a homogeneous process for the detection and/or determination of an analyte in a medium in which it may be present.

The determination of the presence or concentration of circulating organic or biological substances in biological liquids is an important step in the diagnosis of a large number of diseases.

One of the methods commonly used for this determination is based on the formation of a complex between the analyte, i.e. the substance to be detected or determined, and an analyte receptor, which is a substance capable of fixing specifically to the analyte. The complex thus formed is disclosed by a labeled reagent.

This method embraces the so-called processes of immunological determination "by competition" or "by excess", described for example by R. Ekins in "Monoclonal Antibodies and Development in Immunoassay", Elsevier 1981, pp. 3-21. The reagent employed is labeled in particular with the aid of a radioactive element, an enzyme or a luminescent compound, for example a fluorescent, chemiluminescent or phosphorescent compound. We are thus referring to radioimmunological processes, immunoenzymatic processes or immunological processes using luminescence (fluorescence, phosphorescence or chemo-luminescence).

In the so-called processes of immunological determination by competition, the medium in which the target analyte may be present is incubated with a deficit of an analyte receptor in the presence of a given quantity of the labeled analyte.

Competition for the receptor then takes place between the target analyte and the labeled analyte. The fraction containing the bound labeled analyte is then separated from the fraction containing the free labeled analyte, and the quantity of labeled analyte in one or other of the fractions is measured.

In the so-called processes of determination by excess, two receptors are used which have a different specificity for the target analyte, one of the receptors being labeled. These processes also require a step for separating the fraction containing the bound labeled receptor from the fraction containing the free labeled receptor.

To perform the determinations rapidly with a very high sensitivity, various means for dispensing with the separation step have been sought and so-called "homogeneous" processes have been developed.

In the field of immunological determinations using fluorescence, there are relatively few homogeneous processes.

Every homogeneous fluorescence method is based on the fact that the binding of the labeled receptor with the analyte causes a modification of the emission characteristics of the fluorescent molecule.

In fluorescence polarization, for example, the polarization of the emitted light is measured, which varies with the size of the molecular structure carrying the fluorescent molecule.

Another homogeneous process, based on the phenomenon of energy transfer between two chromophores, is described in French Patent 2 282 115. In this process, the transfer of energy from the donor chromophore to the acceptor chromophore takes place if the emission spectrum of the former and the excitation spectrum of the latter overlap (energy compatibility) and if the distance between the two chromophores is in general less than 100 Å. Similarly, the process described in French Patent 2 422 165 uses a chemiluminescent tracer and a quenching agent which is capable of modifying the emission of the light by chemoluminescence when this molecule is at a short but not collision-causing distance, which in general is less than 100 Å.

However, these processes have disadvantages. In the case of polarization, there are limitations associated with the size of the target analyte. In the process which uses energy transfer, both the analyte and the receptor have to be labeled and the emission of the acceptor's luminescence interferes with the measurement of the donor's luminescence. Furthermore, not all pairs of chromophores can be chosen in this case (energy compatibility).

There may also be mentioned the homogeneous processes of determination using fluorescence which are described in U.S. Pat. No. 4,318,707 and European Patent Application 17908 in the name of Syva.

The process described in U.S. Pat. No. 4,318,707 uses particles which are capable of reducing the excitation intensity and/or of reducing the emission intensity of electronically excitable molecules.

The process according to European Patent Application 17908 is based on the capability of distributing a chromogenic substance between a fraction in which the chromogen retains its chromogenic activity and a fraction in which the chromogenic activity is inhibited, the degree of distribution depending on the concentration of the analyte in the medium of determination.

Furthermore, it is known that the presence of a heavy atom, such as an iodine atom, near or within the structure of a fluorescent compound causes its fluorescence to decrease.

This very general effect is described in the literature, for example by E. L. Wehry in "Fluorescence", edited by G. G. Guilbault, M. Dekker, New York 1967. According to the state of the art, this effect is observed when the fluorescent molecule naturally contains a heavy atom, when heavy atoms are introduced chemically into the fluorescent molecule or when heavy atoms are present in solution in the measurement medium. The mechanism of this heavy atom effect is not very well understood in the case where the heavy atom is outside the molecule. However, in the case where the fluorescent molecule contains heavy atoms (naturally present or incorporated chemically), this phenomenon is explained by an increase in the spin-orbit couplings of the said fluorescent molecule compared with its homolog not containing a heavy atom, and this can result in an increase in the non-radiant inter-system transitions $S_1^* \rightsquigarrow T_1^*$ and radiant inter-system transitions $T_1^* \rightarrow S_0$, but also in non-radiant internal conversions $S_1^* \rightsquigarrow S_0$. A decrease in the fluorescence due to the presence of a heavy atom is observed in all cases and a modification of the phosphorescence is observed when the molecules and the conditions of measurement allow. A concrete example of this effect is the decrease in the quantum yield of fluorescein observed when the latter is chemically bonded to polyiodinated molecules such as triiodothyronine ($T_3$) or tetraiodothyronine ($T_4$); this is an internal heavy atom effect.

In the case where the heavy atom is not fixed by chemical bonding to the fluorescent molecule but is present in solution in the measurement medium, it is thought that the increase in the spin-orbit coupling in the luminescent molecule might be due either to collisions of the fluorescent molecule with the heavy atom or to the formation of weak complexes by charge transfer. It actually manifests itself by an increase in the inter-system transitions of the luminescent molecule, $S_1^* \rightsquigarrow T_1^*$ and $T_1^* \rightarrow S_0$, so that although the heavy atom effect results sometimes in an increase and sometimes in a decrease in the intensity of phosphorescent molecules, it always results in a decrease in the intensity of fluorescent molecules.

This internal heavy atom effect has already been utilized in a homogeneous process of determination by fluorimetry. Here, reference may be made to European Patent Application 15695, which describes a process of this type using a conjugate formed between a ligand analog and a fluorescent compound, the ligand analog naturally carrying a heavy atom capable of quenching the said fluorescent molecule, and the said conjugate being covalently bonded to a macromolecular polysaccharide. In this case, the binding of the antibody specific with the molecule containing the heavy atom reduces the inhibition and results in an increase in the fluorescence.

It has now been found that the heavy atom effect can be used to advantage in a homogeneous process for the detection and/or determination of an analyte using luminescence, without the heavy atom being in solution in the measurement medium or fixed to the luminescent molecule.

Surprisingly, it has in fact been found that, in an immunological determination by competition or by excess, an inter-system transition takes place in the luminescent molecule when the luminescent molecule is bound to one of the reagents used, while the other reagent carries units containing at least one heavy atom.

From the general point of view, the present invention therefore relates to a process for the detection and/or determination of an analyte in a medium in which it may be present, by disclosing the reaction product of the analyte and at least one corresponding receptor, which consists in:

1) adding to said medium a first reagent consisting of a receptor for the said analyte;
2) adding a second reagent consisting of at least one of the components of the reaction product of the analyte and at least one of its receptors; one of the two reagents being coupled with a luminescent compound and the other reagent possessing a heavy atom or units containing a heavy atom.
3) incubating said medium after the addition of each reagent or after the addition of both reagents,
4) exciting the resulting medium and
5) measuring at equilibrium or during the kinetics, the signal emitted by the luminescent compound, said signal being modulated by the heavy atom effect.

The following definitions apply in the present description:
"analyte": any substance or group of analogous substances to be detected and/or determined;
"receptor": any substance capable of fixing specifically to a site on the said analyte;
"luminescent compound": any substance which, when excited at a given wavelength or by a given chemical compound, is capable of emitting light;
"heavy atom": an atom of high atomic number, whose presence near a luminescent molecule is capable of causing an increase in the spin-orbit coupling of the latter. Examples which may be determined of heavy atoms suitable for the purposes of the invention are, in particular, halogen atoms, mercury, thallium, lead and silver;
"unit containing at least one heavy atom": any chemical substance which naturally contains at least one heavy atom or to which at least one heavy atom can be fixed.

Furthermore, the expression "component of the reaction product of the analyte and at least one of its receptors" denotes the analyte or at least one of its receptors, depending on the type of method used.

The analyte can be of a biological or non-biological nature. It embraces, in particular, biological substances such as: antibodies, antigens, toxins, enzymes, proteins, for example protein A, hormones, steroids, avidin, biotin, micro-organisms and haptens and non-biological substances capable of binding specifically with a ligand, such as drugs.

Examples of analytes which can be detected by the process of the invention are cited in European Patent Application 17 908, which is incorporated in the present description by way of reference.

Specific examples of such analytes are:
adeno-cortiocotropic hormone (ACTH), anti-diuretic hormone (ADH), aldosterone, albumin, cyclic AMP, androstenedione, angiotensin, anti-thyroglobulin antibodies, carbohydrate antigens CA-125, CA 19-9 and CA 15-3, cortisol, digoxin, digitoxin, estriol, ferritine, gastrine, growth hormone (HGH), placental lactogen hormone (PLH), insulin, methotrexate, myoglobin, parathyrin, pepsinogen, 17 alpha-hydroprogesterone, thyroglobulin, thyroxine binding globlulin, glucagon, trypsin, HBe and Anti-HBe hepatitis, HBs and anti-HBs hepatitis, delta- and anti-delta-particles, transferrin, IgG, IgM, IgA, C3, haptoglobulin, ceruloplasmin, alpha 1 antitrypsine, rheumatoid factor, and more particularly: carbino-embryonic antigen (CEA), alpha-foetoprotein (AFP), estradiol, progesterone, testosterone, thyreostimulant hormone (TSH), tri-iodothyrosine (T3), free triiodothyrosine (FT3), thyroxine (T4), free thyroxine (FT4), prolactine, luteinizing hormone (LH), stimulating folliculo hormone (SFH), total IgE.

The luminescent compound used in the process of the invention can be chosen from the group consisting of fluorescent, chemoluminescent or phosphorescent compounds.

Fluorescent compounds which can be used are any compounds which absorb light at wavelengths above 300 nm, preferably above 400 or 450 nm, and which have an extinction coefficient greater than $10^4$ above 400 nm.

Another class of fluorescent compounds suitable for the purposes of the invention consists in fluorescent rare earth chelates and fluorescent organic molecules with a long life time, such as pyrene derivatives.

Examples of fluorescent compounds suitable for the purposes of the invention are cited in particular in European Patent 1 5 695 and in U.S. Pat. No. 3,998,943, which are incorporated in the present description by way of reference.

The particularly preferred fluorescent compounds are fluorescein, fluorescein isothiocyanate and the rare earth chelates and rare earth cryptates described by the Applicant Company in French Patent Application 84 14 799.

In the process according to the invention, it is also possible to use a chemiluminescent compound, such as luminol and acridinium esters (Methods in Enzymology 1978, 57, 424), or fluorescent compounds, such as fluorescein, excited by the reaction product of an oxalate and hydrogen perioxide (Acc. Chem. Res. 1969, 2, 80).

Phosphorescent compounds, such as, for example, erythrosin and eosine (Biochem. J. 1979, 183, 50), are also suitable as luminescent compounds for the purposes of the invention.

It should be noted that erythrosine and eosine, which are iodinated compounds, may be also used as units containing at least one heavy atom.

The coupling of one of the reagents with the luminescent compound is carried out by conventional coupling processes so as to produce a covalent bond between the said reagent and the luminescent compound. It is also possible to fix the luminescent compound to one of the reagents by adsorption.

The heavy atom present in one of the reagents can be introduced by direct substitution, for example in the case of halogens, by substitution in units present in the biological molecule, such as the aromatic nuclei, or by fixing units containing a heavy atom to the reagent. These units can be fixed by any of the coupling means commonly used for proteins, for example by means of chelating agents or by coupling with a disulfide bridge in the case of mercury, as described in British Patent 2 109 407. Preferably, the heavy atom is an iodine atom introduced into the second reagent by iodination, for example by the process of A. E. Bolton and W. N. Hunter (Biochem. J. 133, 529, 1973).

The heavy atom or the units containing at least one heavy atom may be also fixed on one of the reagents by means of an appropriate molecule containing functions suitable for coupling with said reagent and functions suitable for coupling with the heavy atom or the units containing at least one heavy atom. For instance, a polypeptide may be used as intermediate molecule, such as polylysine, the coupling reactions with the reagent and the heavy atom or the units containing at least one heavy atom being carried out by the conventional coupling methods.

The use of such an intermediate molecule allows to increase the number of heavy atoms by reagent without considerably affecting the immunoreactivity thereof.

Among examples of "units containing at least one heavy atom" are iodinated derivatives of succinimide, such as the following derivatives:

-N- 3-(3,5-diodo-4-hydroxyphenyl)propionyloxy succinimide ester,

-N- 3-(3-iodo-4-hydroxyphenyl)propionyloxy succinimide ester,

-N- 2-(4-iodophenylsulfonamido)acetoxy succinimide ester,

-N- 6-(4-iodophenylsulfonamido)hexyloxy succinimide ester as well as the coupling products of these compounds with a polypeptide, such as polylysine.

These iodinated organic derivatives are directly combined with the reagents used in the process according to the invention by placing them in contact with a solution of said reagent with an appropriate buffer.

The addition of the first and second reagent within the invention process may be simultaneously or stepwise. In the case of a stepwise addition the medium is advantageously incubated between each reagent addition.

The exciting step is carried out either during or after the final incubation step, following which the measurement is effected during the kinetics or at the equilibrium.

This exciting step is carried out with the means of light energy when the luminescent compound is a fluorescent or phosphorescent compound and with the means of appropriate chemical reagents when the luminescent compound is a chemiluminescent.

The exciting step by light energy is effected at a wavelength within the absorption spectrum of the used fluorescent or phosphorescent compound.

It should be noted that the light exciting step may be carried out under a conventional manner or by a pulsed manner, for example according to the process disclosed by Wieder in U.S. Pat. No. 4,058,732. In this later case, it is necessary to use a luminescent compound having a long luminescent (fluorescent or phosphorescent) decay lifetime compared with the decay lifetime of the ambient substances, such as the substances contained in the medium to be assayed and the assay material. Preferably, this decay lifetime should be higher than one microsecond. The excitation duration should be of course lower than the luminescent decay lifetime of the chosen luminescent compound. Advantageously, the rare earth chelates or rare cryptates, such as the ones disclosed in FR patent application 84.14.799 may be used as fluorescent compounds having a long fluorescent decay lifetime (or a high half-lifetime).

On the other hand, it should be noted that the invention process may be carried out in liquid phase and that the measurement of the fluorescence or phosphorescence may be effected after the deposit of the reaction medium on a solid phase, such as a strip, a gel or any other suitable support.

Thus, in the case of an excess method the process of the invention consists in:
1) adding to the medium containing the target analyte a first reagent consisting of a receptor for the said analyte, coupled with a luminescent compound;
2) adding a second reagent consisting of one or more additional receptor for the said analyte, the said second reagent possessing a heavy atom or units containing a heavy atom;
3) incubating the medium in the above conditions;
4) exciting the resulting medium and
5) measuring the signal emitted at equilibrium or during the kinetics.

In the case of a competition method, the process of the invention consists in:
1) adding to the medium containing the target analyte a first reagent consisting of a receptor for the said analyte, possessing a heavy atom or units containing a heavy atom;
2) adding a second reagent consisting of the analyte coupled with a luminescent compound;
3) incubating the medium in the above conditions;
4) exciting the resulting medium and
5) measuring the signal emitted at equilibrium or during the kinetics.

According to another alternative embodiment of the process of the invention in the case of a competition method, the medium containing the target analyte is initially incubated with a first reagent consisting of a receptor for the said analyte, the said receptor being coupled with a luminescent compound, and the analyte possessing a heavy atom or units containing a heavy atom is added as a second reagent, the following steps being identical to those defined above.

The process according to the invention is particularly applicable to immunological determinations of antigens or haptens by excess or by competition.

For example, the determination of an antigen or hapten by competition uses, as the first reagent, a corresponding antibody labelled with fluorescein or iodinated, and a given quantity of the iodinated or fluorescein-labelled antigen.

The determination of an antigen or hapten by excess uses two antibodies with different specificities for the target antigen or hapten, one being labelled with fluorescein and the other being iodinated. Of course, in this type of determination, it is also possible to use other fluorescent compounds and other units containing at least one heavy atom, such as those mentioned above.

The present invention also relates to a kit comprising essentially:
- a first reagent consisting of at least one receptor for the analyte to be determined;
- a second reagent consisting of at least one of the components of the reaction product of the analyte and at least one of its receptors, one of the reagents being coupled with a luminescent compound and the other reagent possessing a heavy atom or units containing at least one heavy atom;
- standard samples containing known quantities of the analyte to be determined, for establishing the standard curves or standard range; and
- the diluents or buffers required for the determination.

If the luminescent compound is a chemiluminescent compound, the kit according to the invention also contains the appropriate chemical reagents required for excitation.

Figure 1:
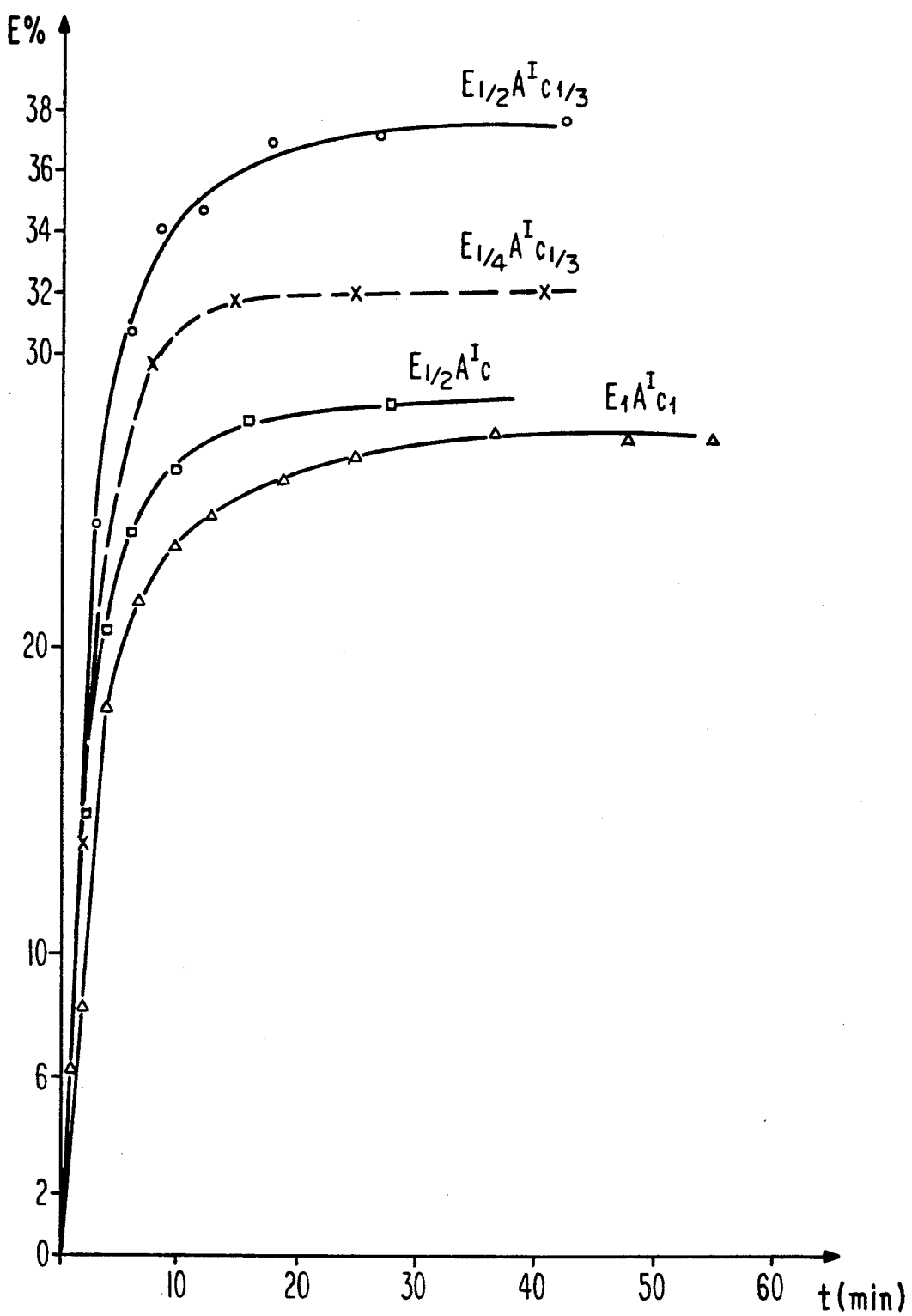
FIG. 1 is a graph of incubation time versus efficiency.

The invention will now be described in greater detail by means of the non-limiting examples below, in which the substance to be detected or determined is an antibody or antigen.

The following compounds were used in these examples:
rabbit gammaglobulins ($\gamma_{RG}$) from Miles;
anti-rabbit sheep gammaglobulins ($\gamma_{ARSG}$) obtained by passing a
sheep antiserum immunized with $\gamma_{RG}$ through a column of DEAE-cellulose;
human serum albumin (HSA) at a concentration of 10 mg/ml in a 0.1M phosphate buffer of pH 7.4;
fluorescein isothiocyanate, isomer I;
hydroxysuccinic ester of 3-(4-hydroxyphenyl) propionic acid (NHSPP: Bolton and Hunter's reagent);
sodium metabisulfite;
1,3,4,6-tetrachloro-3a,6a-diphenylglycoluril as an iodine generator;
Wathman DE 52 DEAE-cellulose as an ion exchanger;
a column of PD 10 Pharmacia filtration gel;
a phosphate buffer (PB);
the fluorescence measurements were made on a PERKIN-ELMER LS 5, 2.5/IO nm slits, with an excitation at 495 nm, an emission at 520 nm and an expansion factor of 15;
the anti-prolactin monoclonal antibodies $E_1$ and 3D3 contained in the kits for the immunoradiometric assays of the prolactin made by the Company ORIS INDUSTRIE SA and available in the market under the name "ELSA PROL" and
the anti-CEA monoclonal antibodies G 12, G 13 and G 15 contained in the kits for the immunoradiometric assays of carcinoembryonic antigen made by the Company ORIS INDUSTRIE SA and available in the market under the name "ELSA CEA".

EXAMPLE 1

Demonstration of the Heavy Atom Effect a) Labelling of $\gamma_{RG}$ With Fluorescein 1.44 mg of the fluorescent compound (FITC) were dissolved in 1 ml of water and the pH was brought to 9.5 with sodium hydroxide.

24 mg of $\gamma_{RG}$ were dissolved in 2 ml of 0.05M phosphate buffer of pH 7.4 and 200 µl of the solution containing the fluorescent compound were added. The reaction was carried out for 2 Hours at room temperature. the pH being kept at 9.5 with dilute sodium hydroxide.

The reaction mixture was then dialyzed overnight against a 0.05M phosphate buffer of pH 7.4.

The solution was then passed through a column of Whatman DE 52 DEAE-cellulose equilibrated with 0.05M phosphate buffer of pH 7.4.

Various fractions were eluted by increasing salinity gradient elution (NaCl). The molar ratio fluorescein/protein ($\gamma_{RG}$) is determined by the formula:

$$F/P = \frac{A_{495}}{\epsilon_{495}} \times \frac{\epsilon_{280} \times 150,000}{A_{280} - 0.35 A_{495}}$$

in which:
$A_X$ is the absorption at wavelength X;
$\epsilon$ represents the molar absorption coefficient;
$\epsilon_{495} = 72,000$; and
$\epsilon_{280} = 1.4$ for 0.1% by weight/volume.

The various fractions obtained according to the salinity of the mobile phase are indicated below:

| [NaCl] | F/P | Approximate concentration of $\gamma_{RG}$ |
|---|---|---|
| 0.05 M | ≅1.3 | 120 µg/ml |
| 0.1 M | ≅2.2 | 140 µg/ml |
| 0.2 M | ≅3.5 | 240 µg/ml |
| 0.4 M | ≅5.5 | 180 µg/ml | b) Labeling of $\gamma_{ARSG}$ With Iodine

This labeling was carried out by the chloramine T method of R. Hunter (Proc. Soc. Exp. Biol. Med. 133(3), 989, 1970). The following were brought into contact for 3 minutes:
200 µl of $\gamma_{ARSG}$ at a concentration of 3.5 mg/ml;
100 µl of KI at a concentration of $10^{-3}$M in water; and 200 μl of chloramine T at a concentration of 10⁻²M in water, and 200 μl of a 10⁻²M aqueous solution of MBS were then added.

The solution obtained was charged onto a PD 10 column equilibrated with 0.05M phosphate buffer of pH 7.5 (pump throughput: 16 ml/h). Detection at the column outlet was effected by measurement of the optical density at 280 nm. The fraction corresponding to the top of the first peak was collected; its concentration of $\gamma_{ARSG}^I$ was evaluated as 0.24 mg/ml.

c) Demonstration of the Effect of the Iodine Atom

Three solutions were prepared:

reference solution:
- 50 μl of 0.1 M PB of pH 7.4
- 200 μl of HSA free solution:
- 50 μl of 0.1 M PB of pH 7.4
- 50 μl of a fraction of $\gamma_{RG}$ labeled with fluorescein ($\gamma_{RG}^F$), diluted to 1/400 in HSA
- 150 μl of HSA bound solution:
- 50 μl of $\gamma_{ARSG}$ labeled with iodine ($\gamma_{ARSG}^I$)
- 50 μl of $\gamma_{RG}^F$ diluted to 1/400 in HSA
- 150 μl of HSA Incubation was carried out for 1 hour 30 minutes, 250 μl of 0.1M phosphate buffer of pH 7.4 were added and the fluorescence was measured for an excitation at 495 nm.

The efficiency E of the inter-system transition was determined by the formula:

$$E = \frac{I \text{ free solution} - I \text{ bound solution}}{I \text{ free solution} - I \text{ reference solution}}$$

in which I is the intensity of fluorescence.

The results obtained with the fraction F/P=3.5 are given in Table I below. They show that 16% of the emission energy of the fluorescein molecule has been transferred in a non-radiant manner. Since the quantity of $\gamma_{ARSG}$ used is an excess quantity, it is considered that all the $\gamma_{RG}$ are bound.

EXAMPLE 2

Use of Polyiodinated Units

Some NHSPP was dissolved in a 1:1 mixture of benzene/acetaldehyde to give a solution containing 1.3·10⁻² mol/l.

The following were brought into contact:

| | |
|---|---|
| NHSPP evaporated at the bottom of a tube | 100 μl |
| $\gamma_{ARSG}$ 200 μl | 3 mg/ml |

The reaction was left to proceed for 15 minutes in ice, after which the following were added:

| | |
|---|---|
| KI (5 · 10⁻¹ M) | 20 μl |
| chloramine T (5 · 10⁻² M) | 20 μl | and 20 μl of 5·10⁻²M MBS were added after 1 minute. The solution was charged onto a PD 10 column; the top of the first peak was collected; it had an optical density of 0.527 at 280 nm. The fluorescence of the three solutions, prepared under the same conditions as in Example 1, was measured for an excitation at 495 nm.

The results, which are given in Table I below, show that the efficiency of the process is enhanced by the use of polyiodinated units.

EXAMPLE 3 a) Preparation of the Iodinated Reagent

The following compounds were brought into contact in a tube:

| | |
|---|---|
| NHSPP (10⁻³ M) | 100 μl |
| KI (10⁻¹ M) | 100 μl |
| chloramine (10⁻² M) | 100 μl |

After a contact time of 3 minutes, 100 μl of MBS (10⁻²M) were added.

Extraction was then carried out with 2×2 ml of benzene containing 20 μl of dimethylformamide. The organic phase was evaporated in another tube and 100 μl of $\gamma_{ARSG}$ were added. The reaction was carried out for 15 minutes in ice. The mixture was deposited on a PD 10 column. The top of the peak collected had an optical density of 0.1 at 280 nm.

b) Demonstration of the Heavy Atom Effect

This fraction of $\gamma_{ARSG}^I$ was used to prepare a bound solution in the same proportions as in Example 1, using the fraction $\gamma_G^F$ 1/400, F/P=3.5.

The reference and free solutions were prepared separately under the same conditions as in Example 1. The results of fluorescence measurement are given in Table I.

EXAMPLE 4

The following were brought into contact:

| | |
|---|---|
| NHSPP, 10⁻² M, evaporated | 100 μl |
| iodine generator in CCl₄, 5 · 10⁻² M, evaporated | 20 μl |
| KI   5.10⁻² M | 20 μl |
| phosphate buffer, 0.05 M, pH 7.4 | 40 μl |

After a contact time of 1 minute, extraction was carried out with 2×1 ml of benzene in dimethylformamide (1%). The organic phase was evaporated in another tube and 10 μl of $\gamma_{ARSG}$ were added, after which the reaction was left to proceed for 15 minutes in ice. The $\gamma_{ARSG}^I$ formed were separated off by dialysis against 1 liter of 0.05M phosphate buffer of pH 7.4.

A 1/10 dilution of $\gamma_{ARSG}^I$ was used to form a free solution and a bound solution with the $\gamma_{RG}^F$, 1/400, F/P=3.5, prepared according to Example 1.

The results obtained are reported in Table I.

TABLE I

| | Solutions tested | | | |
|---|---|---|---|---|
| Example No. | Reference solution | Free solution | Bound solution | Efficiency |
| 1 | 43.5 | 77.9 | 72.4 | 0.16 |
| 2 | 36.7 | 76.6 | 65.2 | 0.286 |
| 3 | 34.4 | 59.4 | 53.9 | 0.21 |
| 4 | 33 | 64.5 | 56.5 | 0.25 |

EXAMPLE 5

The effect of labeling the $\gamma_{RG}$ with fluorescein was evaluated. The $\gamma_{ARSG}$ labeled with iodine according to Example 4 and diluted to 1/20 in HSA, and the various $\gamma_{RG}^F$ fractions prepared in Example 1, were used.

The fluorescence measurements were made according to the procedure of Example 1. The following results were obtained:

| $\gamma_{RG}^F$ fraction, F/P | Bound solution | Free solution | E |
| --- | --- | --- | --- |
| 1.3 | 32.2 | 33.3 | 0.17 |
| 2.2 | 38.5 | 41.5 | 0.20 |
| 3.5 | 53.1 | 62.0 | 0.25 |
| 5.5 | 53.6 | 75.5 | 0.44 |

The fluorescence of the reference solution was 26.8.

It is noted that the effect increases with the number of fluoresceins per $\gamma_{RG}$. This increase is definitely associated with the delocalization of the energy of the excited state of the fluorescein by intermolecular transfer between fluorescein molecules.

EXAMPLE 6

The dilution curve was established for the antibody $\gamma_{ARSG}$ labeled according to the procedure of Example 4 with the $\gamma_{RG}^F$, F/P=5.5, diluted to 1/400.

The following results were obtained:

| Dilution of $\gamma_{ARSG}$ in HSA | I | E % |
| --- | --- | --- |
| 1/10 | 26.6 | 44 |
| 1/20 | 26.7 | 44 |
| 1/100 | 43.2 | 9.4 |
| 1/500 | 46.4 | 2.7 |
| 1/1000 | 47.7 | 0 |

It is noted that the efficiency decreases as the dilution factor increases.

EXAMPLE 7

Use of the Process of the Invention in a Method of Determination by Excess

Labeling of the Anti-Prolactin Monoclonal Antibody $E_1$ with fluorescein 0.5 ml of a solution of $E_1$ containing 9.7 mg/ml was mixed with 0.2 mg of FITC (molecular probe) in 0.5 ml of water. The pH was adjusted to 9.3 with sodium hydroxide. The reaction was left to proceed for 3 hours at room temperature, the pH being kept constant. The solution was then neutralized to pH 7 and dialyzed for 20 hours against 2×2 liters of 0.05M phosphate buffer of pH 7.4.

A column of about 15 ml of DEAE-cellulose gel, equilibrated with 0.05M phosphate buffer of pH 7.4, was made up. The column was charged with the dialyzed reaction medium and elution was carried out with buffers which were respectively 0.05M, 0.1M, 0.2M, 0.4M, 0.7M and 1M in respect of NaCl, the pH being 7.4.

The peaks eluted with the 0.4M NaCl and 0.7M NaCl buffers were collected and dialyzed.

The optical density observed for the peak obtained with the 0.4M NaCl buffer was 0.184 at 280 nm and 0.167 at 495 nm, which corresponds to an approximate antibody concentration of 90 µg/ml and to a ratio F/P of about 4.

b) Labeling of the Monoclonal Antibody 3D3 with Iodine

The protocol is identical to that of Example 4. The following products were used:

| | |
| --- | --- |
| NHSPP ($10^{-2}$ M) | 200 µl |
| iodine generator ($5 \cdot 10^{-2}$ M) | 40 µl |
| KI ($5 \cdot 10^{-2}$ M) | 40 µl |
| phosphate buffer, 0.05 M, pH 7.4 | 40 µl |

Extraction was carried out twice with 1 ml of benzene at a concentration of 1% in dimethylformamide. After evaporation, 200 µl of 3D3 containing 3.3 mg/ml were added and the reaction was left to proceed for 15 minutes in ice. Separation was performed on a column of PD 10 and the fraction having an optical density of 0.485 at 280 nm was recovered; its concentration was 350 µg/ml.

Determination by Excess fluorescent $E_1$ ($E_1^F$) at a concentration of 3 µg/ml in a solution of HSA containing 0.5 mg/ml;

iodine-labeled 3D3 ($3D3^I$) at a concentration of 110 µg/ml in the same solution of HSA;

3D3 at a concentration of 110 µg/ml in the same solution of HSA;

prolactin, PRL, at a concentration of 0.6 µg/ml in the same solution of HSA.

The following three solutions were prepared:

| | |
| --- | --- |
| reference solution: | 50 µl of HSA containing 5 mg/ml |
| bound solution$^I$: | { 50 µl of $E_1^F$ <br> 50 µl of $3D3^I$ <br> 50 µl of PRL |
| bound solution: | { 50 µl of $E_1^F$ <br> 50 µl of 3D3 <br> 50 µl of PRL |

Each solution was incubated for 2 hours at room temperature and 100 µl of HSA and 250 µl of phosphate buffer were added.

The fluorescence measurements made according to the procedure of Example 1 gave the following results:

| | Fluorescence |
| --- | --- |
| reference solution | 29.7 |
| bound solution$^I$ | 197.3 |
| bound solution | 231.1 |
| Δ | 33.8 |
| E | 0.17 |

The same phenomenon is therefore observed in an excess method (Example 7), by labeling two antibodies having different specificities, as in a competition method (Examples 1 to 6).

EXAMPLE 8

Kinetic Study

The determination of Example 7 was repeated at room temperature using a solution of prolactin, PRL, containing 0.6 µg/ml in 100 µl of HSA containing 5 µg/ml, and the same reagents $E_1^F$ and $3D3^I$, but varying their concentration, and the efficiency E of the inter-system transition was measured as a function of the incubation time.

The following concentrations were used:

- $E_1^F$ at a concentration of 3 μg/ml in a solution of HSA containing 5 μg/ml
- $Ac^I = 3D3^I$ at a concentration of 360 μg/ml in a solution of HSA containing 5 μg/ml

- $E_1^F$ at a concentration of 1.5 μg/ml in the same solution of HSA
- $AC^I = 3D3^I$ at a concentration of 360 μg/ml in the same solution of HSA

- $E_1^F$ at a concentration of 0.75 μg/ml in the same solution of HSA
- $Ac_1^I = 3D3^I$ at a concentration of 120 μg/ml in the same solution of HSA

- $E_1^F$ at a concentration of 1.5 μg/ml in the same solution of HSA
- $Ac_1^I$ at a concentration of 120 μg/ml in the same solution of HSA The results obtained are shown on the graph of the attached FIG. 1, on which the incubation time in minutes is plotted on the abscissa and the efficiency E in % on the ordinate.

These results show that the process of the invention can also be used in kinetics.

EXAMPLE 9

Standard Curve

Six solutions of PRL, containing 600, 150, 75, 30, 7.5 and 0 ng/ml in a solution of HSA containing 5 mg/ml, were prepared.

50 μl of each solution were incubated in a tube with 50 μl of $E_1^F$ containing 3 μg/ml and 50 μl of $3D3^I$ containing 120 μg/ml, for 30 minutes at room temperature, and 350 μl of phosphate buffer were added. The inhibition efficiency E was then measured as a function of the value of the standard medium consisting of 150 μl of HSA containing 5 mg/ml, it being known that 1 μU=30 ng.

Figure 2:
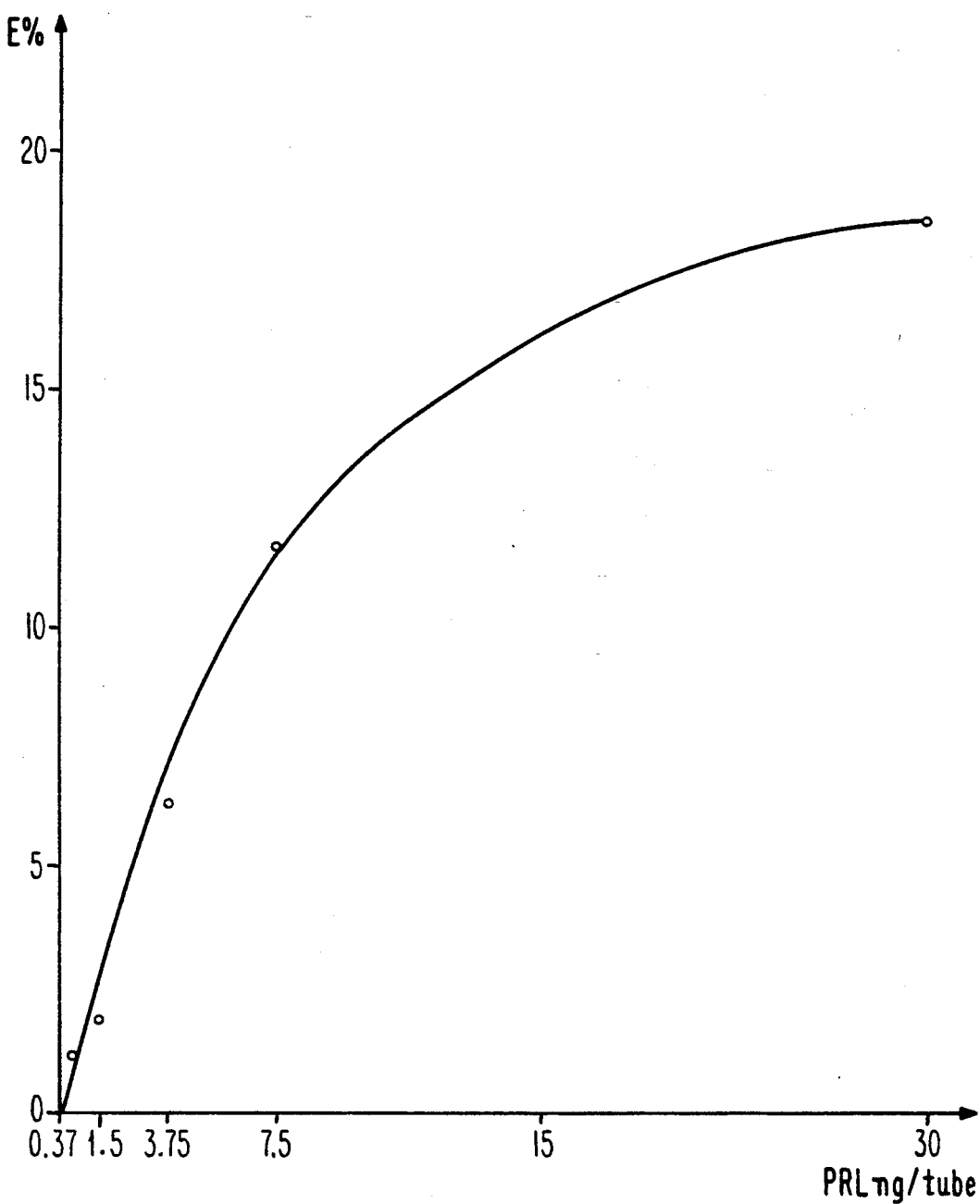
FIG. 2 is a graph of prolactin concentration versus efficiency.

The results obtained are shown on the graph of the attached FIG. 2, on which the concentration of prolactin, PRL, expressed in ng/tube is plotted on the abscissa and the efficiency E in % on the ordinate.

It is thus possible to establish standard curves for each protein to be determined.

EXAMPLE 10

This example was carried out using the anti-CEA antibodies G 12, G 13 and G 15 a) Labeling of the Anti-CEA Antibody G 12 with Fluorescein

The protocol used was the same as in Example 7a. The dialysis and the elution of the column were carried out with 0.01M TRIS buffer of pH 8. The peaks eluted with 0.2 and 0.4M NaCl were recovered. The value of F/P was about 2.75 for the peak eluted at 0.2M. The solution collected was concentrated to 800 μg/ml.

b) Labeling of G 15 with Iodine

The protocol was identical to that of Example 4. The following products were used:

| | |
|---|---|
| NHSPP ($10^{-2}$ M) | 200 μl |
| iodine generator (5 · $10^{-2}$ M) | 40 μl |
| KI (5 · $10^{-2}$ M) | 40 μl |
| phosphate buffer, 0.05 M, pH 7.4 | 40 μl |
| G 15 (5 mg/ml) | 200 μl |

The fraction having an optical density of 0.84 at 280 nm was collected; its concentration was 600 μg/ml.

c) Labeling of G 13 with Iodine

The above procedure was followed and the fraction having an optical density of 0.35 at 280 nm was collected; its concentration was 250 μg/ml.

A standard containing 300 ng of CEA per ml was used.

$G_{12}^F$ was diluted to 1/2000 in HSA containing 5 mg/ml.

$G_{15}^I$ was diluted to 1/6 in HSA.

The following three solutions were prepared:

| | |
|---|---|
| reference solution: | 100 μl of HSA + 100 μl of buffer |
| bound solution: | 50 μl of $G_{12}^F$ diluted to 1/2000<br>50 μl of $G_{15}^I$ diluted to 1/6<br>100 μl of the standard |
| free solution: | 50 μl of $G_{12}^F$ diluted to 1/2000<br>50 μl of $G_{15}^I$ diluted to 1/6<br>100 μl of buffer |

These solutions were incubated for 1 hour at 45° C. and 300 μl of phosphate buffer were added.

The fluorescence of each solution was measured for an excitation at 495 nm, giving the following results:

| Solution | Intensity of florescence | Efficiency |
|---|---|---|
| reference solution: | 44.5 | E = 0.16 |
| bound solution: | 90.5 | ΔF = 8.8 |
| free solution: | 99.33 | |

Therefore, there is also a 16% inhibition when two antibodies of different specificities are bound to the antigen.

The same experiment was carried out with the addition, in a third incubation, of the antibody $G_{13}^I$, the specificity of which is different from that of G 12 and G 15.

The following solutions were tested:

| | |
|---|---|
| bound solution | 50 μl of $G_{12}^F$ diluted to 1/2000<br>50 μl of $G_{15}^I$ diluted to 1/6<br>50 μl of $G_{13}^I$ diluted to ⅓<br>100 μl of the standard |
| free solution | 50 μl of $G_{12}^F$ diluted to 1/2000<br>50 μl of $G_{15}^I$ diluted to 1/6<br>50 μl of $G_{13}^I$ diluted to ⅓<br>100 μl of buffer |

These solutions were incubated for 3×1 hour at 45° C. and 250 μl of phosphate buffer were added. The following results were obtained:

| Solution | Intensity of fluorescence | Efficiency |
|---|---|---|
| reference solution | 81 | 0.41 |
| bound solution | 106.7 | ΔF = 18.2 |
| free solution | 124.9 | |

These results show that the presence of a second iodinated antibody at another site on the antigen increases the inhibition of fluorescence of the fluorescein-labeled antibody G 12.

EXAMPLE 11

Standard Curve

Four solutions of CEA, containing 300, 200, 100 and 0 ng/ml, were prepared. Each solution was incubated with $G_{12}^F$ diluted to 1/3000 in HSA and with $G_{13}^I$ and $G_{15}^I$ diluted respectively to $\frac{1}{8}$ and 1/6 in a solution of HSA, and the fluorescence was measured.

The following results were obtained:

| Solution | Intensity of fluorescence | ΔF | E % |
|---|---|---|---|
| reference solution | 54 | — | — |
| solution containing 300 ng/ml | 65.9 | 11.9 | 0.5 |
| solution containing 200 ng/ml | 68 | 9.8 | 0.41 |
| solution containing 100 ng/ml | 71.8 | 6 | 0.25 |
| solution containing 0 ng/ml | 77.8 | 0 | 0 |

EXAMPLE 12

Use of Iodinated Derivatives of Succinimide as Units Containing at Least One Heavy Atom A. Preparation of Iodinated Derivatives of Succinimide a) Compound 1: N-[3-(3,5-diodo-4-hydroxyphenyl)propionyloxy]succinimide ester of formula

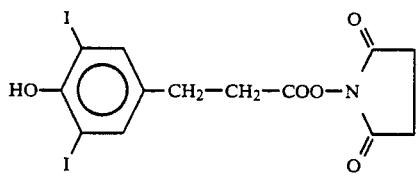

$1 \times 10^{-4}$ moles (26.3 mg) of N-[3-(4-hydroxyphenyl)-propionyloxy]succinimide ester (origin: FLUKA) were dissolved in 2.5 ml of a mixture of benzene and ethyl acetate (50:50 v/v), after what $2.10^{-4}$ moles (86.4 mg) of Iodogen ® (origin: SIGMA) were added in one step, followed by 83 mg of potassium iodide in solution in 100 μl of phosphate buffer 0.05M (pH 7.4); a bright violet color developed instantaneously. The reaction was allowed to continue at 20° C. under stirring for 15 mins (under argon). Then it was stopped by adding a saturated solution of sodium metabisulfite in water until discoloration of the reaction medium. The organic phases were separated by decanting, then dried over anhydrous MgSO4 and evaporated in vacuo. The residue was taken up in CH2Cl2 or in anhydrous benzene.

The product was then purified by silica gel chromatography. The eluent was a discontinuous gradient of benzene/ethyl acetate. The expected product was eluted for a mixture of benzene and ethyl acetate (90:10 v/v). The purity of Compound 1 was controlled by C.C.M. (eluent:toluene/ethyl acetate 1/1 v/v) and compared with a control; RF=0.7. The elementary analysis and mass spectrometry were found to be in conformity with the structure of the product. Yield: 58%.

b) Compound 2: N-[3-(3-iodo-4-hydroxyphenyl)propionyloxy]succinimide ester of formula

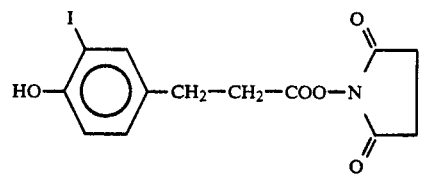

It was proceeded as described above for compound 1, using the following ingredients in the proportions indicated hereunder:

| | |
|---|---|
| N-[3-(4-hydroxyphenyl) propionyloxy]succinimide ester: | $2.10^{-3}$ moles (0.526 g) |
| Iodogen$^R$ (Sigma): | $2.10^{-3}$ moles (0.864 g) |
| KI: | $4.10^{-3}$ moles (0.584 g) in 500 μl of phosphate buffer 0.05 M (pH: 7.4) |

The resulting product was put through the same purifying and control stages as compound 1.

c) Compound 3: N-[2-(4-iodophenylsulfonamido)acetoxy]succinimide ester of formula

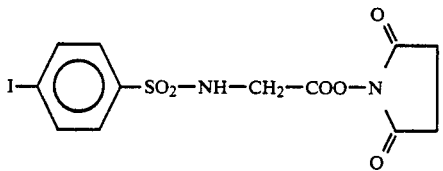

The synthesis of compound 3 was made in two separate stages after purification and isolation from intermediate product A, according to the following reaction diagram:

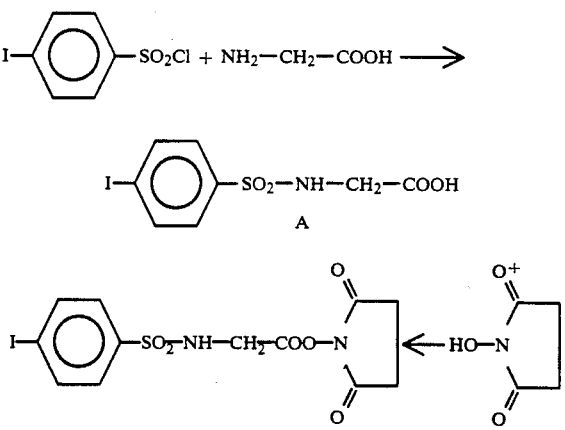

Compound 3

Synthesis of A $8.10^{-3}$ moles (2.4 g) of p-iodophenylsulfochloride in solution in 5 ml of dioxan were added dropwise to $7.10^{-3}$ moles (0.525 g) of glycocoll in aqueous solution adjusted beforehand by sodium hydroxide 1M (10 ml) at pH 9 and cooled in an ice bath. When the addition is completed, the ice bath is removed and the reaction is allowed to continue for one hour at 20° C. under stirring. (The pH was controlled with a pH meter and readjusted to pH 9 throughout the reaction).

At the end of the reaction, the mixture was diluted with twice its own volume of distilled water. The solution was freed of any reaction insoluble materials by filtration. The filtrate was acidified dropwise under stirring at pH 2 with hydrochloric acid 6N. The expected condensation product precipitated profusely in white flakes. The crude product was filtered, then washed several times in distilled water, then dewatered and dried in vacuo in a drier in the presence of $P_2O_5$ for a whole night. Yield: 73% (1.75 g).

The purity of the product was controlled by C.C.M. and by the conventional spectrophotometric methods.

Synthesis of Compound 3

To a solution of 2 mmoles of A (0.682 g) and 2 mmoles of N-hydroxysuccinimide (0.230 g) in 10 ml of THF, cooled beforehand to 0° C., were added in one step, 2 mmoles of dicyclohexylcarbodiimide (DCC) (0.412 g). The reaction mixture was stirred and kept for one hour at that temperature. After that period of time, the cooling bath was removed and the reaction mixture was filtered on fritted glass No. 3, and the filtrate evaporated in vacuo. The residue, constituted of a white foam, was taken up with $CH_2Cl_2$, filtered on Celite ®  then re-evaporated in vacuo. The resulting crude product was recrystallized in $CH_2Cl_2$. Weight obtained: 0.371 g; Yield: 42%. The product was identified by the conventional spectrophotometric methods and its composition confirmed by centesimal analysis.

d) Compound 4: N-[6-(4-iodophenylsulfonamido)hexyloxy]succinimide ester of formula

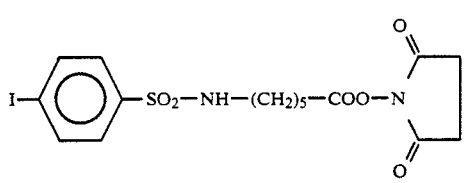

The synthesis of Compound 4 was conducted in two stages after isolation of the intermediate product B and according to the following reaction diagram:

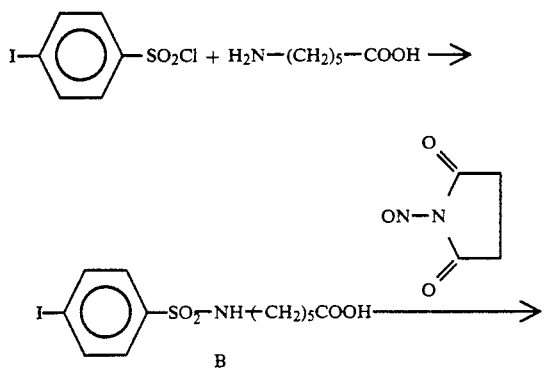

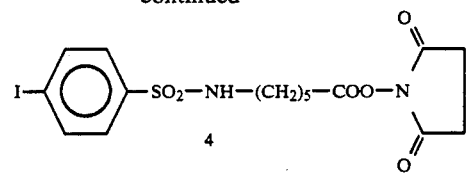

1) Synthesis of B 5 mmoles (1.52 g) of p-iodophenylsulfochloride in solution in 5 ml of dioxan were added dropwise to an aqueous solution of 7 mmoles (0.918 g) of 5-amino caproic acid (Fluka), adjusted beforehand to pH9 with 10 ml of NaOH 1M and cooled with an ice bath.

After the addition of the iodinated reagent, the ice bath was removed and the reaction was allowed to continue for 3 hours at 20° C. (the pH was also controlled throughout the reaction as in the preceding example).

The reaction mixture was then filtered on fritted glass No. 3 and the filtrate was acidified to pH 4 with a few drops of HCl 12N. The expected product B then precipitated profusely. Said product was filtered, washed on the filtered with a lot of distilled water, de-watered and finally dried in a drier in vacuo over $P_2O_5$ for a whole night. Weight obtained: 1.30 g; Yield: 68%. The purity of the product was controlled by C.C.M. (silica) eluent: $CHCl_3$/Methanol (3:1 v/v). M.P. was: 154°±1° C. The structure of the product was confirmed by centesimal analysis.

2) Synthesis of Compound 4

It was proceeded as indicated for compound 3, using the following ingredients:

| product B: | 2 mmoles (0.762 g) |
|---|---|
| N-hydroxysuccinimide: | 3 mmoles (0.345 g) |
| D.C.C.: | 3 mmoles (0.614 g) |
| THF solvent: | 10 ml. |

The reaction time was one hour at 4° C. and one night at 20° C.

The purification of the product was identical to that of Compound 3. Weight obtained: 0.840 g; Yield: 91%. Purity was controlled by C.C.M. (eluent ethyl acetate/$CH_2 Cl_2$ (1:1) and by centesimal analysis. The structure of the product was determined by spectrophotometry I.R. and by mass spectrometry. This was found to be conformed to the structure expected for the described compound 4.

B. Coupling of Succinimide Derivatives with Antibodies

Antibody 3D3 (anti-prolactine antibody) was used in this example.

$1.10^{-6}$ mole of 3D3 (10 mg/ml) in solution in 200 µl of phosphate buffer 0.05M (pH: 7.4) and 200 µl of borate buffer 0.01 M(pH: 9) were added to 2 mg of iodinated regaent 1 (compound 1) dissolved beforehand in $CH_2Cl_2$ and evaporated under argon so as to create a coating on the walls of the reaction tube. The coupling reaction was allowed to continue under stirring for one hour at 20° C. After that period of time, the iodine-marked 3D3 was then purified by chromatography on a colum of PD 10 and the peak corresponding to the marked antibody (void volume, of the column) was isolated. Its concentration was then measured by its absorbing power at 280 nm.

The isolated marked antibody was used at the concentration of 150 μg/ml in the fluorescence inhibition test.

It was proceeded as indicated for compounds 3 and 4.

Following a similar process compound 2 was coupled with anti-CEA antibody G 15. For this purpose, antibody G 15 (200 μl at 6.5 mg/ml) were put into contact with 200 μl of compound 2 (1.24 mg in 3.75 ml of $CH_2Cl_2$, then 200 μl evaporated at the bottom of the tube) and 200 μl of borate buffer (pH 9). The mixture was incubated for 1 h 30 min at the ambient temperature.

C. Dosage by Excess of the Prolactine

The reagents used, are as follows:
$3D_3^I$ antibody: 150 μg/ml by dilution in HSA at 5 g/l;
$E_1^F$ antibody diluted at 1/100° [1 μg/ml] in solution in rabbit gammaglobulins at the concentration of 5 mg/ml.
prolactine antigen (supplied by Immunotech); 0.5 μg/ml in solution in HSA at 5 g/l.

Diluents:
Rabbit gammaglobulin (concentration 5 g/l) in solution in phosphate buffer 50 mM (pH 7.4)
HSA (concentration 5 g/l) in phosphate buffer 50 mM
Control: HSA (5 g/l)+eluting solution of purification (50:50 v/v)

The three following solutions were prepared:

| | |
|---|---|
| control solution: | 50 μl of $\gamma_{GL}$ |
| | 50 μl ofd HSA |
| | 50 μl of control |
| bound solution: | 50 μl of $E_1^F$ |
| | 50 μl of prolactine |
| | 50 μl of $3D_3^I$ |
| free solution: | 50 μl of $E_1$ |
| | 50 μl of HSA |
| | 50 μl of $3D_3^I$ |

Each solution was incubated for one hour, at 20° C. Then, before making any readings, 350 μl of phosphate buffer 0.05M (pH: 7.4.) were added to each one.

The fluorescence measurements were made at 496 nm (excitation) and 520 nm (emission) with a fluorometer and the efficacity E was determinated.

The results obtained are given in the following table.

D. Determination by Excess of CEA Antigen

The above method was repeated using CEA antigen instead of prolactine and the following reagents:
iodinated reagent: The solution obtained under point B with compound 2. Said solution was ajusted to 0.10 mg/ml after the purification on PD 10.
Fluorescent reagent: solution of G 12 labelled with fluoresceine and diluted to 1/2000.

The incubation was carried out for two hours at 45° C. The obtained results are also in the following table.

| Dosage of | Iodinated derivative | Iodinated derivative $3D_3$ mole/mole | Coupling reaction pH | measured E % |
|---|---|---|---|---|
| PROLAC-TINE | Coumpound 1 | 10/1 | 9.0 | 11 |
| | | 50/1 | 9.0 | 18 |
| | | 300/1 | 9.0 | 16.5 |
| | Coumpound 3 | 30/1 | 9.0 | 8.2 |
| | | 100/1 | 9.0 | 9 |
| | Compound 4 | 30/1 | 7.4 | 2.3 |
| | | 100/1 | 7.4 | 5 |
| | | 100/1 | 9.0 | 7 |
| CEA | Compound 2 | 20/1 | 9.0 | 11 |

EXAMPLE 13

Use of the Coupling Product Between a Polypeptide and an Iodinated Organic Molecule as Units Containing at Least One Heavy Atom In this example the coupling product between the polylysine and diiodinated compound 1 was prepared; said coupling product is hereinunder named reagent A.

This reagent A may be represented the following statistic formula:

$$NH_2^- CH-CO\!\!\left(\!\!NH-CH-CO\!\right)_{\!\!n}\!\!NH-CH-COOH$$

with side chains $(CH_2)_2-NH_2$, $(CH_2)_2-NH_2$, and $$(CH_2)_2-NH\!\!\left[\!CO\!\left(CH_2\right)_2\!\!-\!\!\underset{I}{\underset{|}{\bigcirc}}\!\!-OH\right]_k$$

in which
n=327
k=50

A. Synthesis of Reagent A 5 mg (1.04 $10^{-7}$ moles) of polylysine chlorhydrate (M.W=48000) supplied by Sigma Chemicals were dissolved in 500 of borate buffer 0.01M pH 8.9; the pH of the resulting solution was thereafter ajusted to 12 with sodium hydroxide (0.5M) and added to 2.7 μg (5.2 1 $0^{-6}$ moles) of above compound 1 previously deposited on the bottom of a test tube by evaporation of a solution of said compound 1 into $CH_2Cl_2$. The reaction was continued for one hour at 20° C. under agitation.

The product reaction was eluted on PD 10 (Sephadex G 25) with a phosphate buffer 50 mM. The recovered fractions were concentrated up to 90 μl volume by centrifugation.

B. Coupling of Reagent A with Antibody $3D_3$

I 20 μl of phosphate buffer 25 mM pH 5 were added to 80 μl of reagent A and thereafter 100 μl of a solution of carbodiimide (2 mg/ml of water).

After 2 or 3 minutes, 400 μl of a solution of antibody $3D_3$ (200 μl of $3D_3$ at 9.6 mg/ml in phosphate buffer 50 mM, pH 7.4+200 μl of phosphate buffer 200 mM pH 8)

The incubation was effected for 1 hour at 20° C., then one night at 4° C. and 1 hour at 20° C.

The separation was carried out on a column of PD 10 using phosphate buffer 50 mM pH 7.4 as eluting agent.

From the void volume of the column was collected a solution (1 ml) having an optical density of 0.742 at 280 nm. The antibody concentration of this solution was estimated to be 530 μg/ml. Said evolution was submitted to the fluorescence inhibition test described in example 12.

The fluorescence intensities of the different solutions were as follows:

| Reference solution: | 16 |
|---|---|
| bound solution: | 134 |
| free solution: | 150 |
| The efficacity E was: | 11.9% |

What is claimed is:

1. A homogeneous process for the detection or determination of an analyte in a medium in which it may be present by disclosing the reaction product of the analyte and a corresponding receptor comprising the steps of
  a) adding to said medium a first reagent consisting of a receptor for said analyte;
  b) optionally incubating said medium after addition of said first reagent;
  c) adding to said medium a second reagent consisting of at least one of said analyte and said receptor for analyte, one of said first and second reagents being coupled with a luminescent compound and the other of said first and second reagents possessing a heavy atom or units containing a heavy atom;
  d) incubating said medium after addition of said second reagent to produce a resulting medium;
  e) exciting said resulting medium to produce luminescence;
  f) measuring said luminescence at equilibrium or under kinetic conditions, wherein said heavy atom is capable of modulating said luminescence in a medium in which analyte is present, wherein said modulation is by inter-system transition within said luminescent compound and wherein there is substantially no overlap between an absorption spectrum of said heavy atom and an emission spectrum of said luminescent compound, and
  g) comparing said luminescence to a standard in order to determine the presence or concentration of analyte in said medium.

2. The process of claim 1 characterized by being an excess process of determination or detection wherein said first reagent is coupled with a luminescent compound and wherein said second reagent consists of at least one additional receptor for said analyte and possesses a heavy atom or units containing a heavy atom.

3. The process of claim 1 characterized by being a competition process of determination or detection wherein said first reagent possesses a heavy atom or units containing a heavy atom and wherein said second reagent consists of said analyte coupled with a luminescent compound.

4. The process of claim 1 characterized by being a competition process of determination or detection wherein said first reagent is coupled with a luminescent compound and wherein said second reagent consists of said analyte and possesses a heavy atom or units containing a heavy atom.

5. The process according to claim 1, 2, 3, or 4 wherein the analyte is selected from the group consisting of antibodies, antigens, toxins, enzymes, proteins, hormones, steroids, avidin, biotin, micro-organisms and haptens.

6. The process according to claim 1, 2, 3 or 4 wherein the analyte is a drug.

7. The process according to claim 1, 2, 3, or 4 wherein the analyte is prolactin or a carcinoembryonic antigen.

8. The process according to claim 1, 2, 3, or 4 wherein the luminescent compound is a fluorescent, chemiluminiscent, or phosphorescent compound.

9. The process according to claim 5 wherein the luminescent compound is a fluorescent, chemiluminescent, or phosphorescent compound.

10. The process according to claim 7 wherein the luminescent compound is a fluorescent compound selected from the group consisting of fluorescein, rare earth cryptates and chelates.

11. The process according to claim 1, 2, 3, or 4 wherein one of said first and second reagents is labelled with fluorescein and the other of said first and second reagents is iodinated.

12. The process according to claim 1, 2, 3, or 4 wherein the luminescent compound has a luminescent decay lifetime longer than said medium and wherein the excitation of the resulting medium is a pulsed excitation.

13. The process according to claim 5 wherein the luminescent compound is a rare earth cryptate.

14. The process according to claim 2 for the determination or detection of an analyte in a medium, wherein said analyte is an antigen or a hapten and wherein said first reagent is a fluorescein-labelled first antibody for said antigen or hapten and said second reagent is an iodinated second antibody, in less than excess amount, for said antigen or hapten, said first and second antibodies having different specificities for the antigen or hapten.

15. The process according to claim 2 for the determination or detection of an analyte in a medium, wherein said analyte is an antigen or a hapten and wherein said first reagent is a fluorescein-labelled first antibody, in less than excess amount, for said antigen or hapten and said second reagent is an iodinated second antibody for said antigen or hapten, said first and second antibodies having different specificities for the antigen or hapten.

16. The process according to claim 3 for the determination or detection of an analyte in a medium, wherein said analyte is an antigen or a hapten and wherein said first reagent is an iodinated antibody for said antigen or hapten and said second reagent is the antigen or hapten, in a given quantity, labelled with fluorescein.

17. The process according to claim 4 for the determination or detection of an analyte in a medium, wherein said analyte is an antigen or a hapten and wherein said first reagent is a fluorescein-labelled antibody for said antigen or hapten and said second reagent is the iodinated antigen or hapten in a given quantity.

18. The process according to claim 14, 15, 16, or 17 wherein the light excitation of the resulting medium is a pulsed excitation.

19. A kit for the homogeneous detection or determination in liquid phase of an analyte in a medium in which it may be present by measuring luminescence of a luminescent compound, the kit comprising
  a) a first reagent consisting of at least one receptor for the analyte to be determined;
  b) a second reagent consisting of at least one of said analyte and said receptor for analyte, one of said first and second reagents being coupled with said luminescent compound and the other of first and second reagents possessing a heavy atom or units containing at least one heavy atom, said heavy atom being capable of modulating the light emitted by said luminescent compound upon excitation, said modulation being by inter-system transition within said luminescent compound and wherein there is substantially no overlap between an absorption spectrum of said heavy atom and an emission spectrum of said luminescent compound; and c) standard samples containing known quantities of the analyte to be determined, for establishing standard curves.

20. The kit of claim 19 further comprising a diluent and a buffer.

21. The kit according to claim 19 wherein the luminescent compound is a chemiluminescent compound and wherein the kit further comprises chemical reagents capable of producing light excitation.

22. The kit of claim 19, 20, or 21 for the determination or detection of prolactin or a carcinoembryonic antigen, wherein said standard samples contain known quantities of prolactin or a carcinoembryonic antigen.

* * * * *

UNITED STATES PATENT AND TRADEMARK OFFICE
CERTIFICATE OF CORRECTION

PATENT NO. : 5,279,943

DATED : January 18, 1994

INVENTOR(S) : Gerard Mathis and Thierry Davin

It is certified that error appears in the above-identified patent and that said Letters Patent is hereby corrected as shown below:

Column 1, line 37, delete "chemo-luminescence" and insert -- chemiluminescence --

Column 2, line 14, delete "chemo-luminescence" and insert -- chemiluminescence --

Column 4, line 55, delete "chemoluminescent" and insert -- chemiluminescent --

Column 5, line 13, delete "perioxide" and insert -- peroxide --

Column 7, line 48, insert -- Detailed Description of the Invention --

Column 10, line 31, delete "$\gamma_G^F$", insert -- $\gamma_{RG}^F$ --

Column 12, line 21, insert -- c) -- before "Determination by Excess"

Column 12, line 23, delete "0.5" and insert -- 5 --

Column 12, line 32, delete "50 $\mu l$" and insert -- 150 $\mu l$ --

Column 14, line 28, insert -- twice -- after "incubated"

Column 15, line 47, delete "what" and insert -- which --

UNITED STATES PATENT AND TRADEMARK OFFICE
CERTIFICATE OF CORRECTION

PATENT NO. : 5,279,943

DATED : January 18, 1994

INVENTOR(S) : Gerard Mathis and Thierry Davin

It is certified that error appears in the above-indentified patent and that said Letters Patent is hereby corrected as shown below:

Column 18, line 61, delete "0.0I" and insert -- 0.01 --

Column 18, line 62, delete "regaent" and insert -- reagent --

Column 18, line 68, delete "colum" and insert -- column --

Column 19, line 35, delete "ofd" and insert -- of --

Column 20, lines 48 and 49, delete "5.2 I0$^{-6}$" and insert -- 5.2 10$^{-6}$ --

Column 20, line 58, delete "I 20 µl" and insert -- 120 µl --

Column 22, line 57, delete "light"

Signed and Sealed this

First Day of August, 1995

Attest:

BRUCE LEHMAN

Attesting Officer     Commissioner of Patents and Trademarks